US012733857B2

(12) United States Patent
Katsuhara et al.

(10) Patent No.: US 12,733,857 B2
(45) Date of Patent: Sep. 15, 2026

(54) BIOPOTENTIAL MEASUREMENT ELECTRODE AND BIOLOGICAL INFORMATION MEASUREMENT DEVICE

(71) Applicant: SONY GROUP CORPORATION, Tokyo (JP)

(72) Inventors: Mao Katsuhara, Kanagawa (JP); Ryo Sasaki, Kanagawa (JP)

(73) Assignee: Sony Group Corporation, Tokyo (JP)

( * ) Notice: Subject to any disclaimer, the term of this patent is extended or adjusted under 35 U.S.C. 154(b) by 244 days.

(21) Appl. No.: 18/547,907

(22) PCT Filed: Jan. 25, 2022

(86) PCT No.: PCT/JP2022/002536

§ 371 (c)(1),
(2) Date: Aug. 25, 2023

(87) PCT Pub. No.: WO2022/185781

PCT Pub. Date: Sep. 9, 2022

(65) Prior Publication Data

US 2024/0130655 A1 Apr. 25, 2024
US 2024/0225509 A9 Jul. 11, 2024

(30) Foreign Application Priority Data

Mar. 2, 2021 (JP) ................................ 2021-032893

(51) Int. Cl.
*A61B 5/256* (2021.01)
*A61B 5/268* (2021.01)

(52) U.S. Cl.
CPC ............. *A61B 5/256* (2021.01); *A61B 5/268* (2021.01)

(58) Field of Classification Search
CPC ............................. A61B 5/256; A61B 5/6803
See application file for complete search history.

(56) References Cited

U.S. PATENT DOCUMENTS

2007/0225585 A1* 9/2007 Washbon ............... A61B 5/291 600/383
2012/0041292 A1* 2/2012 Ko .......................... A61B 5/24 600/372
2017/0071495 A1* 3/2017 Denison ................ A61B 5/291
(Continued)

FOREIGN PATENT DOCUMENTS

JP H05-15907 1/1993
JP 2008-086390 4/2008
(Continued)

OTHER PUBLICATIONS

International Search Report and Written Opinion prepared by the Japan Patent Office on Apr. 5, 2022, for International Application No. PCT/JP2022/002536, 3 pgs.

*Primary Examiner* — Linda C Dvorak
*Assistant Examiner* — William Mossbrook
(74) *Attorney, Agent, or Firm* — SHERIDAN ROSS P.C.

(57) ABSTRACT

An electrode of an embodiment of the present disclosure includes: a substrate on which an electrical circuit is mounted; a first electrode unit disposed on the substrate and electrically coupled to the electrical circuit; and a second electrode unit having conductivity and elasticity and in which at least a part of the first electrode unit is embedded, the second electrode unit being to be brought into contact with a living body.

15 Claims, 9 Drawing Sheets

(56) References Cited

U.S. PATENT DOCUMENTS

| | | | | |
|---|---|---|---|---|
| 2018/0348863 | A1* | 12/2018 | Aimone | G06F 3/016 |
| 2020/0187859 | A1 | 6/2020 | Yoshioka et al. | |
| 2021/0121113 | A1 | 4/2021 | Katsuhara et al. | |

FOREIGN PATENT DOCUMENTS

| | | |
|---|---|---|
| JP | 2014-033871 | 2/2014 |
| JP | 2018-187359 | 11/2018 |
| JP | 2019-136055 | 8/2019 |
| JP | 2019-198448 | 11/2019 |
| WO | WO-2020095589 A1 | 5/2020 |

* cited by examiner

BIOPOTENTIAL MEASUREMENT ELECTRODE AND BIOLOGICAL INFORMATION MEASUREMENT DEVICE

CROSS REFERENCE TO RELATED APPLICATIONS

This application is a national stage application under 35 U.S.C. 371 and claims the benefit of PCT Application No. PCT/JP2022/002536, having an international filing date of 25 Jan. 2022, which designated the United States, which PCT application claimed the benefit of Japanese Patent Application No. 2021-032893, filed 2 Mar. 2021, the entire disclosures of each of which are incorporated herein by reference.

TECHNICAL FIELD

The present disclosure relates to a biopotential measurement electrode and a biological information measurement device including the same.

BACKGROUND ART

For example, PTL 1 discloses a biometric electrode device where a rubber electrode unit having conductivity is disposed on one surface of a support substrate and a signal processing circuit is disposed on the other surface, the rubber electrode unit and the signal processing circuit being electrically coupled through a conductive thread penetrating the support substrate.

CITATION LIST

Patent Literature

PTL 1: Japanese Unexamined Patent Application Publication No. 2019-136055

SUMMARY OF THE INVENTION

Meanwhile, an electroencephalograph including a resin flexible electrode has recently been developed. However, since the flexible electrode, which is to be brought into contact with a living body, and a substrate where a signal processing circuit such as an impedance conversion circuit is mounted are mechanically coupled mainly with a metal clasp or the like, occurrence of a body motion is likely to make the electrical coupling between the flexible electrode and the substrate unstable. Thus, it has been desired to improve a reliability of an electrical coupling portion between the flexible electrode and the substrate.

Accordingly, it is desirable to provide a biopotential measurement electrode and a biological information measurement device that are in user-friendly forms and are electrically and mechanically highly reliable.

A biopotential measurement electrode of an embodiment of the present disclosure includes: a substrate on which an electrical circuit is mounted; a first electrode unit disposed on the substrate and electrically coupled to the electrical circuit; and a second electrode unit having conductivity and elasticity and in which at least a part of the first electrode unit is embedded, the second electrode unit being to be brought into contact with a living body.

A biological information measurement device of an embodiment of the present disclosure includes the biopotential measurement electrode of the above-described embodiment of the present disclosure.

In the biopotential measurement electrode of the embodiment of the present disclosure and the biological information measurement device of the embodiment of the present disclosure, at least a part of the first electrode unit disposed on the substrate on which the electrical circuit is mounted is embedded in the second electrode unit having conductivity and elasticity and that is to be brought into contact with a living body. This increases a contact area between a substrate side and the second electrode.

MODES FOR CARRYING OUT THE INVENTION

Figure 1:
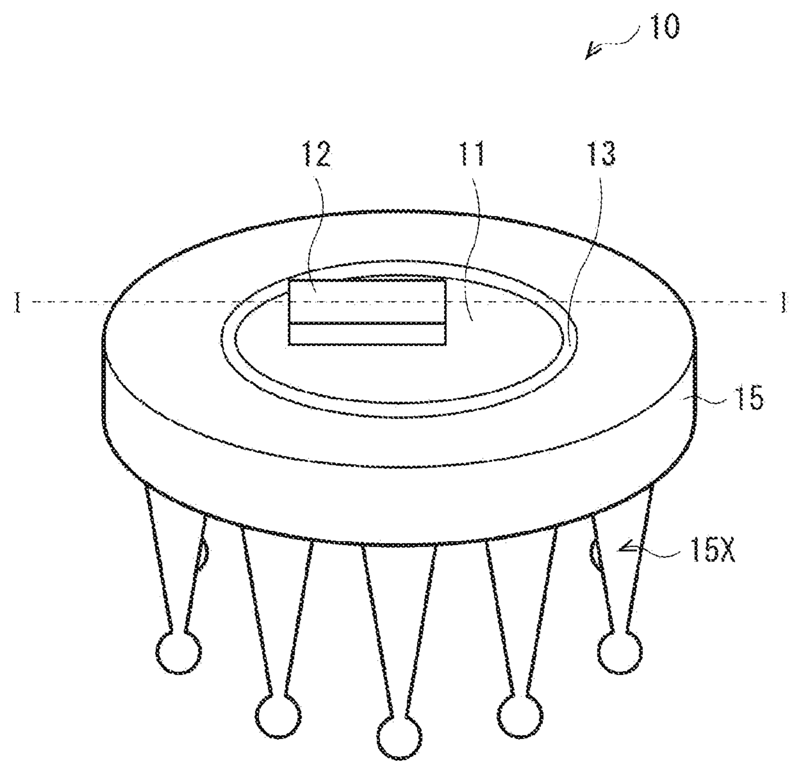
FIG. 1 is a perspective diagram illustrating a configuration of a biopotential measurement electrode according to an embodiment of the present disclosure.

A detailed description will be made below on an embodiment of the present disclosure with reference to the drawings. The description below is merely a specific example of the present disclosure and the present disclosure is by no means limited to a mode below. In addition, the present disclosure is by no means limited by locations, dimensions, dimensional ratios, and the like of components illustrated in the drawings. It should be noted that description will be given in the following order.

1. Embodiment (an example where a substrate with a coupling electrode extending on a plurality of surfaces is embedded in a measurement electrode)
   1-1. Configuration of Biopotential Measurement Electrode
   1-2. Method of Manufacturing Measurement Electrode
   1-3. Configuration of Biological Information Measurement Device
   1-4. Workings•Effects
2. Modification Examples
   2-1. Modification Example 1 (an example where an electrical circuit and a coupling electrode are directly coupled)
   2-2. Modification Example 2 (an example where a substrate and an electrical circuit are embedded in a measurement electrode)
   2-3. Modification Example 3 (an example where a coupling electrode is disposed only on a back surface of a substrate)
   2-4. Modification Example 4 (an example where a part of a substrate is embedded)
   2-5. Modification Example 5 (an example where a coupling electrode includes two members)
   2-6. Modification Example 6 (another example of a shape of a coupling electrode)
   2-7. Modification Example 7 (an example where a part of a coupling electrode is embedded in a measurement electrode)
3. Application Examples

1. Embodiment

Figure 2:
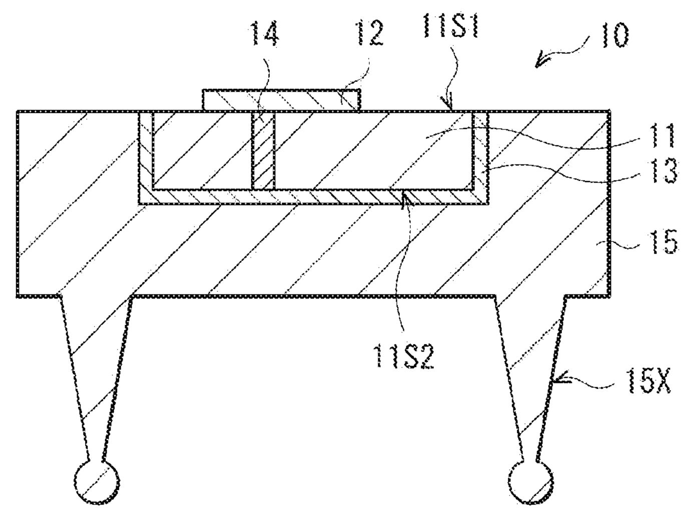
FIG. 2 is a cross-sectional schematic view of the biopotential measurement electrode illustrated in FIG. 1.

FIG. 1 is a perspective diagram illustrating an example of a configuration of a biopotential measurement electrode (a biopotential measurement electrode 10) according to an embodiment of the present disclosure. FIG. 2 schematically illustrates a cross-sectional configuration of the biopotential measurement electrode 10 corresponding to a I-I line seen in FIG. 1. The biopotential measurement electrode 10 is intended to be used as, for example, an electrode for a device that detects biological information regarding a living body (a biological information measurement device 1, see FIG. 3). The biopotential measurement electrode 10 of the present embodiment includes a substrate 11 on which, for example, an electrical circuit 12 is mounted and that is provided with a coupling electrode 13 over a plurality of surfaces, the substrate 11 being embedded in a measurement electrode 15 that is to be brought into contact with a living body. It should be noted that FIG. 1 and FIG. 2 schematically illustrate an example of the configuration of the biopotential measurement electrode 10 and a dimension or a shape therein may be different from actual one.

1-1. Configuration of Biopotential Measurement Electrode

The biopotential measurement electrode 10 includes the substrate 11, the electrical circuit 12, the coupling electrode 13, a through electrode 14, and the measurement electrode 15. The substrate 11 corresponds to a specific example of a "substrate" of the present disclosure and the electrical circuit 12 corresponds to a specific example of an "electrical circuit" of the present disclosure. In addition, the coupling electrode 13 corresponds to a specific example of a "first electrode unit" of the present disclosure and the measurement electrode 15 corresponds to a specific example of a "second electrode unit" of the present disclosure.

The substrate 11 has a pair of opposite surfaces (a front surface 11S1 and a back surface 11S2) and a side surface 11S3 between the front surface 11S1 and the back surface 11S2. The electrical circuit 12 is mounted on the substrate 11. The coupling electrode 13 is formed over, for example, the back surface 11S2 and the side surface 11S3 of the substrate 11. The electrical circuit 12 and the coupling electrode 13 are electrically coupled to each other through the through electrode 14 penetrating, for example, between the front surface 11S1 and the back surface 11S2 of the substrate 11. The measurement electrode 15 includes an elastic body having conductivity and that is deformable along, for example, a living body. In the present embodiment, the substrate 11 is embedded in the measurement electrode 15, which causes the substrate 11 (specifically, the coupling electrode 13) to be electrically in contact with the measurement electrode 15 at a plurality of surfaces.

The substrate 11 is a stacked substrate where, for example, the front surface 11S1 and the back surface 11S2 have wiring line structures and respective wiring lines disposed on a front surface 11S1 side and a back surface 11S2 side are electrically coupled to each other through a via (for example, the through electrode 14).

The electrical circuit 12 includes, for example, a voltage follower circuit including an operational amplifier. In addition to the above, the electrical circuit 12 may include a circuit including R/C nearby for the purpose of, for example, countermeasure against oscillation, impedance adjustment, and filtering. Specifically, the electrical circuit 12 includes later-described switch element 121, variable resistance element 122, AC current source 123, differential circuit 124, amplifier circuit 125, ADC (Analog-Digital Converter) 126, signal processing circuits 127,129, buffer circuit 128, and the like (for example, see FIG. 4).

The coupling electrode 13 is formed over the back surface 1152 and the side surface 1153 of the substrate 11 as described above. The coupling electrode 13 includes, for example, a conductive metal material such as aluminum (Al), copper (Cu), or gold (Au).

The measurement electrode 15 is a dry electrode that is to be brought into contact with a skin of a living body in a dry environment. The measurement electrode 15 has elasticity and is, for example, less than 10 GPa in Young's modulus, preferably, for example, less than 1 GPa. The measurement electrode 15 includes a resin material, which is added with conductivity by, for example, kneading a conductive material such as carbon particles or metal particles.

Examples of the resin material include thermoplastic resins such as polyvinyl chloride (PVC), polypropylene (PP), polyethylene (PE), polyurethane (PU), polyacetal (POM), polyamide (PA), polycarbonate (PC), and copolymers thereof. In addition to the above, thermosetting elastomers such as a silicone resin and a polyurethane resin are also usable. Alternatively, natural rubbers and diene rubbers such as a styrene-butadiene rubber and an isoprene rubber are usable.

Examples of the carbon particles include particles, flakes, or fibers of carbon black (graphite), carbon nanotube, and graphene. Examples of the metal particles include gold (Au), silver (Ag), and copper (Cu). In addition to the above, metal sulfides such as copper sulfide and silver chloride, metal selenides such as copper selenide and silver selenide, and metal chlorides such as copper chloride and silver chloride are usable.

In addition to the above, particles provided by metal-coating polymer particles of PPS resin, PET resin, PES resin, PAI resin, acrylic resin, PVDF resin, epoxy resin, polylactic resin, nylon resin, urethane resin, or the like may be used. Conductive polymers such as PEDOT-PSS, polypyrrole, polyacetylene, polyphenylenevinylene, polythiol, polyaniline, and copolymers and analogs thereof may be dispersed.

An outline of the measurement electrode 15 is not limited to a particular one and can have any shape such as a domed shape, a pyramid shape, or a comb shape in addition to a flat shape. The measurement electrode 15 may further have a plurality of projections 15X on a contact surface 15S1 for a living body. This makes it possible to achieve a favorable contact with, for example, a skin having body hair such as head hair.

1-2. Method of Manufacturing Measurement Electrode

The measurement electrode 15 of the present embodiment can be manufactured, for example, as follows.

First, a conductive carbon black (TOKABLACK manufactured by TOKAI CARBON CO., LTD.) is coated with PEDOT-PSS to contain it, thereby obtaining the conductive particles. Subsequently, a conductive elastomer is obtained by kneading the conductive particles with a thermoelastic polyurethane elastomer at 30 wt %.

Meanwhile, a glass epoxy substrate (the substrate 11) with the front surface 1151 on which the electrical circuit 12, which includes the voltage follower circuit, is mounted is produced. Subsequently, the coupling electrode 13 is formed on the back surface 1152 and the side surface 11S3 of the substrate 11.

Next, after the front surface 11S1 of the substrate 11, on which the electrical circuit 12 is mounted, is protected with a transient resin coating film, the substrate 11 is set in a molding frame and subjected to injection molding with a conductive elastomer. In this manner, the measurement electrode 15 having a desired shape and in which the substrate 11 is embedded is obtained. Then, after the resin coating film is removed, the biopotential measurement electrode 10 and a biopotential measurement instrument are coupled through a wiring line connector.

It should be noted that the above-described manufacturing method is merely by way of example and any other method can be employed for manufacturing.

1-3. Configuration of Biological Information Measurement Device

Figure 3:
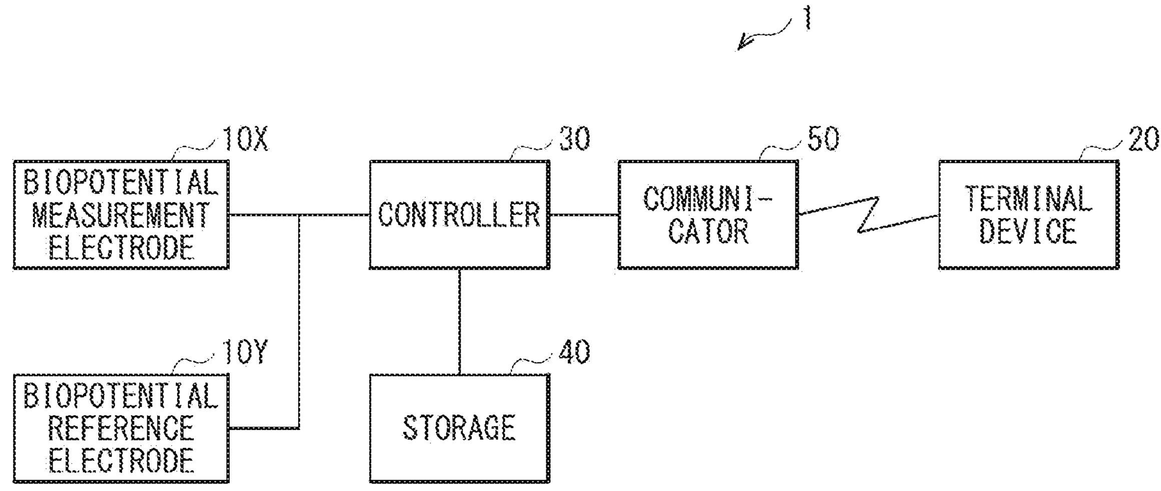
FIG. 3 is a block diagram illustrating a schematic configuration of the biological information measurement device.

FIG. 3 illustrates a schematic configuration of the biological information measurement device 1. The biological information measurement device 1 is a device that detects biological information regarding a living body 1000. Examples of the biological information include a brain wave, an electrical activity of a heart, and an electrical activity of an eye. The living body 1000, which is typically a human being, may be an animal. The biological information measurement device 1 is, for example, wearable equipment such as a head mounted display.

The biological information measurement device 1 is coupled to a network. The network is, for example, a communication line such as LAN or WAN. A terminal device 20 is coupled to the network. The biological information measurement device 1 is configured to be able to communicate with the terminal device 20 via the network. The terminal device 20, which is, for example, a mobile terminal, is configured to be able to communicate with the biological information measurement device 1 via the network.

The terminal device 20 includes, for example, an input unit, a controller, a display unit, and a communicator. The input unit receives input information from a user. The controller sends the input information inputted to the input unit to the biological information measurement device 1 via the communicator. The communicator receives, for example, image data from the biological information measurement device 1 via the network. The controller generates an image signal on the basis of the image data received by the communicator and outputs it to the display unit. The display unit displays the image data on the basis of the image signal inputted from the controller.

The biological information measurement device 1 includes, for example, one or a plurality of biopotential measurement electrodes 10X and biopotential reference electrodes 10Y, a controller 30, a storage 40, and a communicator 50.

Figure 4:
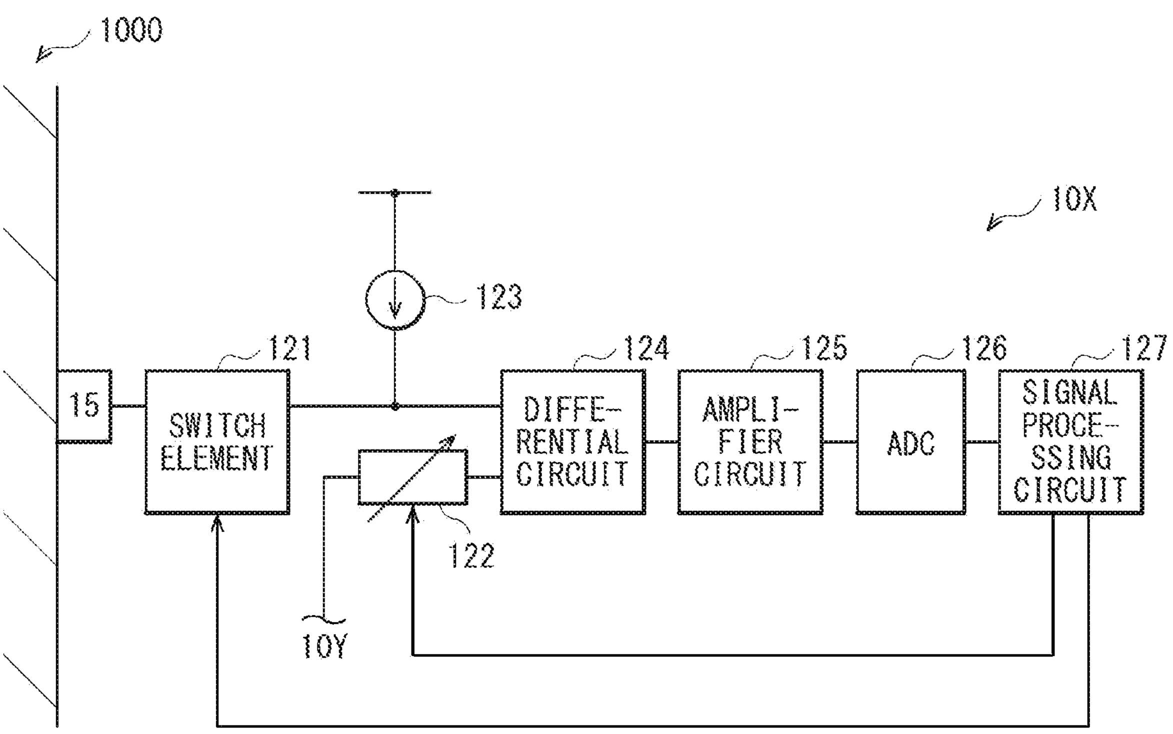
FIG. 4 is a diagram illustrating a circuit configuration of the biopotential measurement electrode.
Figure 5:
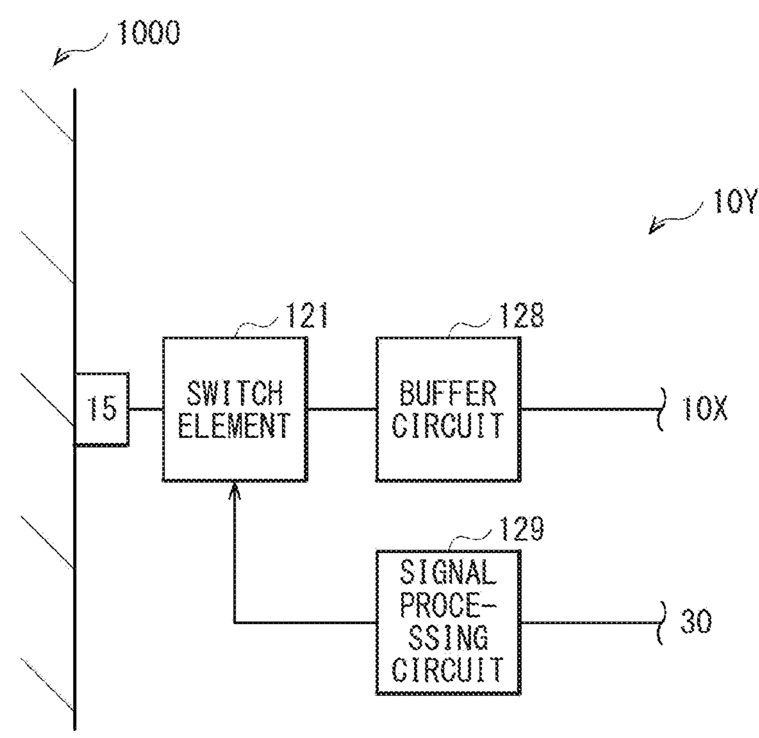
FIG. 5 is a diagram illustrating a circuit configuration of a biopotential reference electrode.

FIG. 4 illustrates an example of a circuit configuration of the biopotential measurement electrode 10X. FIG. 5 illustrates an example of a circuit configuration of the biopotential reference electrode 10Y. The biopotential measurement electrode 10X corresponds to the above-described biopotential measurement electrode 10. The biopotential reference electrode 10Y, which is a reference electrode for the biopotential measurement electrode 10X, has, for example, a configuration similar to that of the above-described biopotential measurement electrode 10.

The biopotential measurement electrode 10X further includes the switch element 121, the variable resistance element 122, the AC current source 123, the differential circuit 124, the amplifier circuit 125, the ADC (Analog-Digital Converter) 126, and the signal processing circuit 127. The biopotential reference electrode 10Y further includes the switch element 121, the buffer circuit 128, and the signal processing circuit 129. It should be noted that the buffer circuit 128 may be omitted.

The switch elements 121 of the biopotential measurement electrode 10X and the biopotential reference electrode 10Y switch ON/OFF the respective measurement electrodes 15 on the basis of control signals from the signal processing circuits 127,129. The switch element 121 of the biopotential measurement electrode 10X is used to adjust a contact impedance between the measurement electrode 15 of each of the biopotential measurement electrode 10X and the biopotential reference electrode 10Y and the living body 1000.

The variable resistance element 122 is disposed between the measurement electrode 15 of the biopotential reference electrode 10Y and the differential circuit 124. Specifically, the variable resistance element 122 is inserted in series with respect to a wiring line between an output end of the buffer circuit 128 and an input end of the differential circuit 124. The variable resistance element 122 is used for adjustment of an impedance difference between input terminals of the differential circuit 124. A resistance value of the variable resistance element 122 is set on the basis of the control signal from the signal processing circuit 127.

The AC current source 123 is coupled to a wiring line between an output end of the switch element 121 and the input end of the differential circuit 124. The AC current source 123 supplies an AC current to the measurement electrode 15 of the biopotential measurement electrode 10X. The AC current source 123 is used to measure a contact impedance between the measurement electrode 15 of the biopotential measurement electrode 10X and the measurement electrode 15 of the biopotential reference electrode 10Y and the living body 1000.

The differential circuit 124 generates a biological signal corresponding to a difference between a measurement signal obtained from the measurement electrode 15 of the biopotential measurement electrode 10X and a reference signal obtained from the measurement electrode 15 of the biopotential reference electrode 10Y. The differential circuit 124 has two input ends coupled to the output end of the switch element 121 and the variable resistance element 122. The differential circuit 124 removes common mode noise (alternating current noise) contained in the measurement signal by using the reference signal.

The amplifier circuit 125 amplifies the biological signal inputted from the differential circuit 124. The ADC 126 converts the biological signal inputted from the amplifier circuit 125 from an analog signal to a digital signal and outputs the biological signal in a form of a digital signal to the signal processing circuit 127.

The signal processing circuit 127 applies a predetermined process to the biological signal of the biopotential measurement electrode 10X and outputs a resulting biological signal to the controller 30.

The signal processing circuit 127 switches the contact impedance between the measurement electrode 15 of the biopotential measurement electrode 10X and the living body 1000 by controlling the switch element 121 on the basis of a control signal from the controller 30. Further, the signal processing circuit 127 switches the impedance difference between the input terminals of the differential circuit 124 by controlling the variable resistance element 122 on the basis of the control signal from the controller 30.

The signal processing circuit 127 sets the contact impedance between the measurement electrode 15 of the biopotential measurement electrode 10X and the living body 1000 at a predetermined value by performing a control on the switch element 121 on the basis of a set value 41 read out of the storage 40. In the biopotential measurement electrode 10X, the signal processing circuit 127 further sets the impedance difference between the input terminals of the differential circuit 124 at a predetermined value by performing a control on the variable resistance element 122 on the basis of a set value read out of the storage 40.

The buffer circuit 128, which is, for example, in a form of a voltage follower, performs impedance conversion. The output end of the buffer circuit 128 is electrically coupled to the input end of the differential circuit 124 of the biopotential measurement electrode 10. This makes it possible to reduce a variation in a voltage value of a signal (the reference signal) subjected to the impedance conversion by the buffer circuit 128 depending on the number of the differential circuits 124 coupled to the output ends of the buffer circuits 128. The signal processing circuit 129 switches the contact impedance between the measurement electrode 15 of the biopotential reference electrode 10Y and the living body 1000 by controlling the switch element 121 on the basis of a control signal from the controller 30. Further, the signal processing circuit 129 adjusts the impedance difference between the input terminals of the differential circuit 124 by controlling the variable resistance element 122 on the basis of the control signal from the controller 30.

The controller 30 generates predetermined image data on the basis of a biological signal SigA obtained by the biopotential measurement electrode 10X. The communicator 50 sends the image data generated by the controller 30 to the terminal device 20 via the network. The storage 40 stores, for example, the set value for the switch element 121 of the biopotential measurement electrode 10X, the set value for the switch element 121 of the biopotential reference electrode 10Y, and the set value for the variable resistance element 122. Further, the controller 30 controls the switch element 121 and the variable resistance element 122 of the biopotential measurement electrode 10X and the switch element 121 of biopotential reference electrode 10Y by outputting control signals to the signal processing circuit 127 and the signal processing circuit 129.

1-4. Workings•Effects

The biopotential measurement electrode 10 of the present embodiment includes the substrate 11 on which the electrical circuit 12 is mounted and that is provided with the coupling electrode 13 over the plurality of surfaces, the substrate 11 being embedded in the measurement electrode 15. This causes the substrate 11 side and the measurement electrode 15 to be in contact at the plurality of surfaces. This will be described below.

A biological information measurement device that performs measurement of a biopotential such as a brain wave or measurement of a bioimpedance such as an electrical activity of skin usually includes an electrode called a wet electrode, which reduces a contact impedance with a living body by using a gel for measurement, saline, or the like.

However, the wet electrode is difficult to use for a consumer purpose in terms of contamination of a user, temporal change, and user-unfriendliness. Accordingly, development of a biological information measurement device including a dry-type electrode called a dry electrode has recently been advanced. While being easy to fit, the dry electrode has a contact impedance as large as 10 kΩ to 100 kΩ. Accordingly, to reduce a decrease in signal quality due to noise, a reduction in impedance is achieved by disposing an impedance conversion circuit at a distance as electrically close as possible from the electrode. Such an electrode is called an active electrode.

The active electrode is in a form of a flexible electrode including an elastomer, such as rubber, blended with conductive particles, such as carbon, in terms of fitness (comfortableness). The flexible electrode and a substrate where a signal processing circuit including the impedance conversion circuit is formed are usually coupled using a mechanical metal clasp. Consequently, occurrence of a body motion is likely to make the electrical coupling between the flexible electrode and the substrate unstable. In addition, such a coupling manner, which significantly limits the biological information measurement device in shape and usability, becomes a factor for lowering a flexibility of enclosure design.

In contrast, according to the present embodiment, the substrate 11 on which the electrical circuit 12 is mounted and that is provided with the coupling electrode 13 over the plurality of surfaces is embedded in the measurement electrode 15 having conductivity and elasticity. This causes the coupling electrode 13 and the measurement electrode 15 to be in contact at the plurality of surfaces with an increased contact area.

By virtue of the above, the biopotential measurement electrode 10 of the present embodiment has an improved contact area between the substrate 11 side and the measurement electrode 15 as compared with a case where they are mechanically coupled using a metal clasp or the like as described above, allowing for ensuring an electrical coupling between the substrate 11 side and the measurement electrode 15. In other words, a biopotential can be accurately measured and a reliability against stresses from a plurality of directions is improved. Therefore, it is possible to provide the biopotential measurement electrode 10 that is in a user-friendly form and is electrically and mechanically highly reliable.

In addition, in the biopotential measurement electrode 10 of the present embodiment, the substrate 11, on which the electrical circuit 12 is mounted, is embedded in the measurement electrode 15, which makes it possible to reduce a space for a coupling portion between the substrate 11 side and the measurement electrode 15 as compared with they are mechanically coupled using a clasp as described above. Therefore, it is possible to downsize the biopotential measurement electrode 10. This makes it possible to improve the fitness of the biological information measurement device 1.

Next, description will be made on Modification Examples 1 to 7 and application examples of the above-described embodiment. Hereinbelow, a component similar to that of the above-described embodiment is assigned with the same reference sign and the description thereof is omitted, if necessary.

2. Modification Examples

2-1. Modification Example 1

Figure 6:
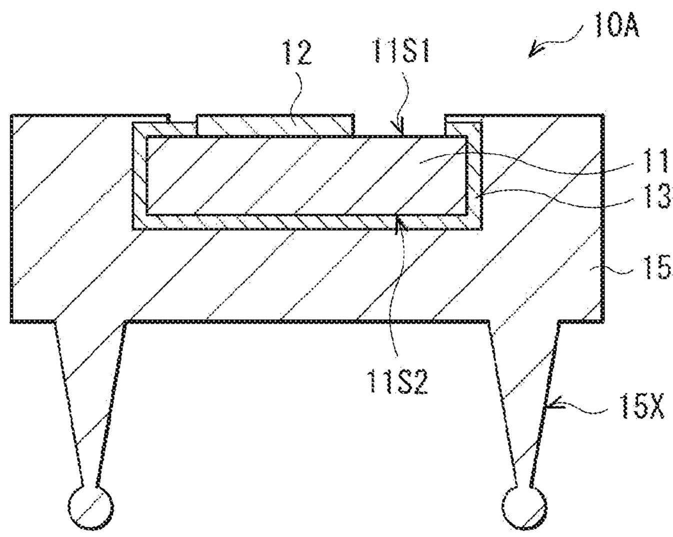
FIG. 6 is a cross-sectional schematic diagram illustrating a configuration of a biopotential measurement electrode according to Modification Example 1 of the present disclosure.

FIG. 6 schematically illustrates a cross-sectional configuration of a biopotential measurement electrode (a biopotential measurement electrode 10A) according to Modification Example 1 of the present disclosure. The biopotential measurement electrode 10A is intended to be used as, for example, an electrode for a device (the biological information measurement device 1) that detects biological information regarding a living body as in the above-described embodiment. The biopotential measurement electrode 10A of the present modification example is different from the above-described embodiment in that the coupling electrode 13 is formed to extend from the back surface 11S2 to the side surface 11S3 and the front surface 11S1 of the substrate 11 with a part (for example, a peripheral portion) of the front surface 11S1 of the substrate 11 covered by the measurement electrode 15.

By virtue of forming the coupling electrode 13 from the back surface 11S2 to the front surface 11S1 and embedding the substrate 11 to cause the measurement electrode 15 to cover the coupling electrode 13 disposed on the front surface 11S1 of the substrate 11 as described above, the contact area between the substrate 11 side and the measurement electrode 15 is further increased. Therefore, it is possible to further improve the electrical and mechanical reliability.

In addition, regarding the electrical coupling between the electrical circuit 12 and the coupling electrode 13, for example, a part of the coupling electrode 13 formed on the front surface 11S1 of the substrate 11 may be further extended to the electrical circuit 12 to be electrically coupled not via the through electrode 14 as illustrated in FIG. 6.

2-2. Modification Example 2

Figure 7:
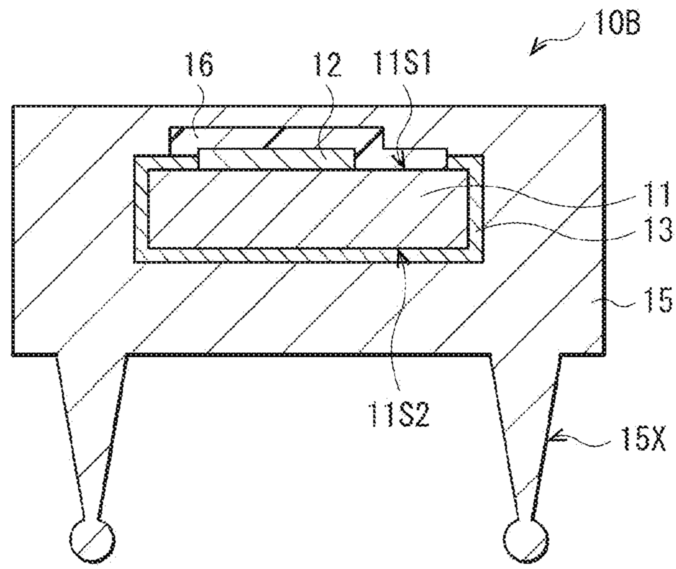
FIG. 7 is a cross-sectional schematic diagram illustrating a configuration of a biopotential measurement electrode according to Modification Example 2 of the present disclosure.

FIG. 7 schematically illustrates a cross-sectional configuration of a biopotential measurement electrode (a biopotential measurement electrode 10B) according to Modification Example 2 of the present disclosure. The biopotential measurement electrode 10B is intended to be used as, for example, an electrode for a device (the biological information measurement device 1) that detects biological information regarding a living body as in the above-described embodiment. The biopotential measurement electrode 10B of the present modification example is provided by, in addition to the configuration of Modification Example 1, protecting the front surface 11S1 of the substrate 11 and the electrical circuit 12 using a passivation film 16 and embedding a while of the substrate 11 in the measurement electrode 15.

This further increases the contact area between the substrate 11 side and the measurement electrode 15. Therefore, it is possible to further improve the electrical and mechanical reliability.

2-3. Modification Example 3

Figure 8:
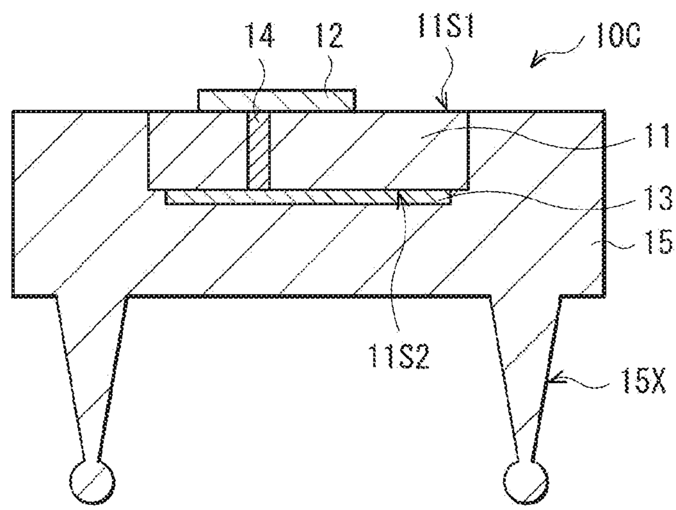
FIG. 8 is a cross-sectional schematic diagram illustrating a configuration of a biopotential measurement electrode according to Modification Example 3 of the present disclosure.

In the above-described embodiment, the example where the coupling electrode 13 is disposed over the back surface 11S2 and the side surface 11S3 of the substrate 11 is described but is not limiting. For example, the coupling electrode 13 may be formed only on the back surface 11S2 of the substrate 11 as in a biopotential measurement electrode 10C illustrated in FIG. 8.

2-4. Modification Example 4

Figure 9:
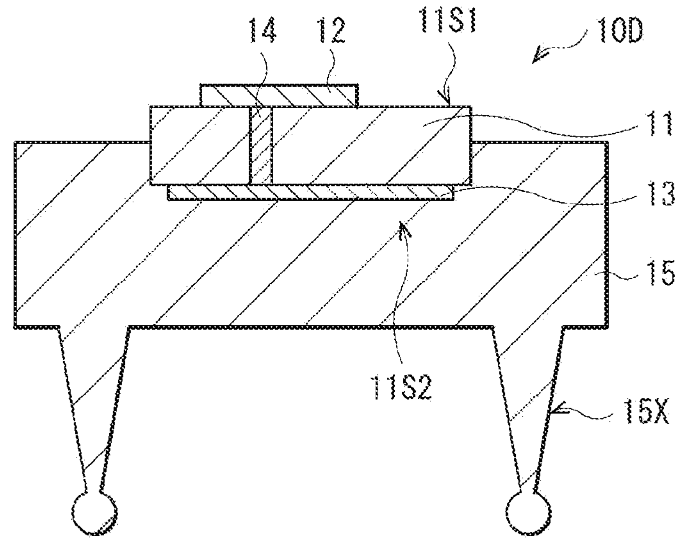
FIG. 9 is a cross-sectional schematic diagram illustrating a configuration of a biopotential measurement electrode according to Modification Example 4 of the present disclosure.

In addition, for example, in the above-described configuration of Modification Example 3 described above, a part of the substrate 11 may be embedded in the measurement electrode 15 as in a biopotential measurement electrode 10D illustrated in FIG. 9.

2-5. Modification Example 5

Figure 10:
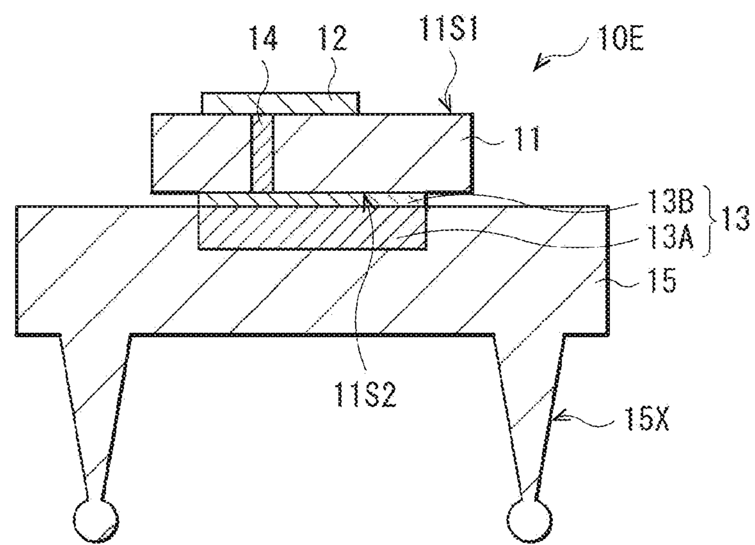
FIG. 10 is a cross-sectional schematic diagram illustrating a configuration of a biopotential measurement electrode according to Modification Example 5 of the present disclosure.

FIG. 10 schematically illustrates a cross-sectional configuration of a biopotential measurement electrode (a biopotential measurement electrode 10E) according to Modification Example 5 of the present disclosure. The biopotential measurement electrode 10E is intended to be used as, for example, an electrode for a device (the biological information measurement device 1) that detects biological information regarding a living body as in the above-described embodiment. The biopotential measurement electrode 10E of the present modification example is different from the above-described embodiment in that the coupling electrode 13 includes two members (a first conductive portion 13A and a second conductive portion 13B), one of which (the first conductive portion 13A) is embedded in the measurement electrode 15.

The coupling electrode 13 of the present modification example includes the two members, the first conductive portion 13A and the second conductive portion 13B, as described above. The first conductive portion 13A is embedded in the measurement electrode 15. The second conductive portion 13B is disposed on the back surface 11S2 of the substrate 11.

The first conductive portion 13A and the second conductive portion 13B each include a magnetic conductive body. The first conductive portion 13A, which is embedded in the measurement electrode 15, is formed as a magnet electrode for magnetic adsorption of the second conductive portion 13B. Specifically, for example, permanent magnets such as an alloy magnet, a ferrite magnet, and a rare-earth magnet are usable as the first conductive portion 13A. Examples of the alloy magnet include a manganese-aluminum magnet and a platinum magnet. Examples of the rare-earth magnet include a neodymium magnet and a praseodymium magnet. In a case where the first conductive portion 13A is formed as a magnet electrode, the second conductive portion 13B includes a ferromagnet. Examples of the ferromagnet include iron (Fe), cobalt (Co), nickel (Ni), Permalloy, alnico, and stainless steel.

The measurement electrode 15 of the present modification example can be manufactured, for example, as follows.

First, a conductive carbon black (TOKABLACK manufactured by TOKAI CARBON CO., LTD.) is coated with PEDOT-PSS to contain it, thereby obtaining the conductive particles as in the above-described embodiment. Subsequently, a conductive elastomer is obtained by kneading the conductive particles with a thermoelastic polyurethane elastomer at 30 wt %.

Next, a substrate-shaped magnet having an entire surface subjected to, for example, a nickel-plating process is produced as the first conductive portion 13A. Subsequently, the magnet is set in a molding frame and subjected to injection molding with a conductive elastomer. In this manner, the measurement electrode 15 having a desired shape and in which the first conductive portion 13A is embedded is obtained.

Next, the second conductive portion 13B is placed on the back surface 11S2 of the substrate 11 and electrically coupled to the electrical circuit 12 (specifically, for example, the through electrode 14) using, for example, solder. Then, the substrate 11 and the measurement electrode 15 are electrically joined by magnetic forces of the first conductive portion 13A and the second conductive portion 13B formed therein, respectively.

It should be noted that the above-described manufacturing method is merely by way of example and any other method can be employed for manufacturing.

In the present modification example, the coupling electrode 13 includes the two members (the first conductive portion 13A and the second conductive portion 13B), the first conductive portion 13A is embedded in the measurement electrode 15, and the second conductive portion 13B is disposed on the back surface 11S2 of the substrate 11 as described above. Further, the first conductive portion 13A is in a form of a magnet electrode and the second conductive portion 13B includes a ferromagnet. This causes the substrate 11 (specifically, the second conductive portion 13B) and the measurement electrode 15 to be electrically joined by a magnetic force, which makes it possible to replace only the measurement electrode 15 in, for example, electrode replacement. Therefore, it is possible to improve convenience and economic efficiency (costs) of the biological information measurement device 1 and reduce an environmental load in addition to the effects of the above-described embodiment.

2-6. Modification Example 6

Figure 11:
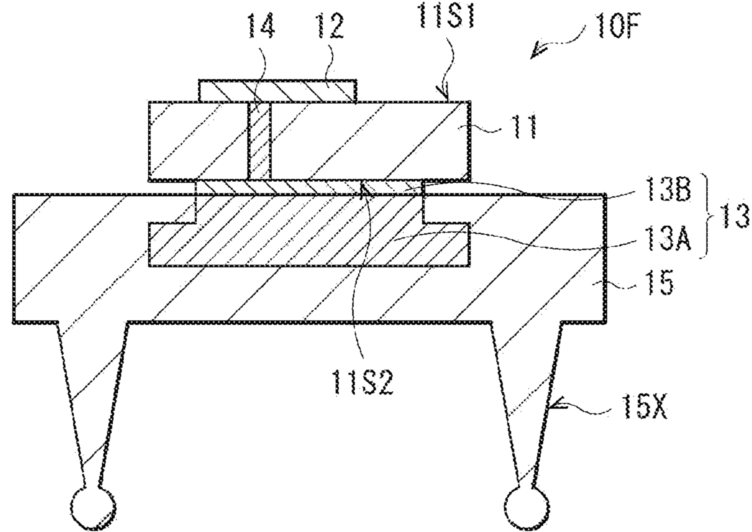
FIG. 11 is a cross-sectional schematic diagram illustrating a configuration of a biopotential measurement electrode according to Modification Example 6 of the present disclosure.

FIG. 11 schematically illustrates a cross-sectional configuration of a biopotential measurement electrode according to Modification Example 6 of the present disclosure (a biopotential measurement electrode 10F). Regarding the above-described first conductive portion 13A embedded in the measurement electrode 15, for example, the part embedded in the measurement electrode 15 may be formed wider than a part exposed on a front surface of the measurement electrode 15 as illustrated in FIG. 11. This makes it possible to prevent detachment of the first conductive portion 13A from the measurement electrode 15.

2-7. Modification Example 7

Figure 12:
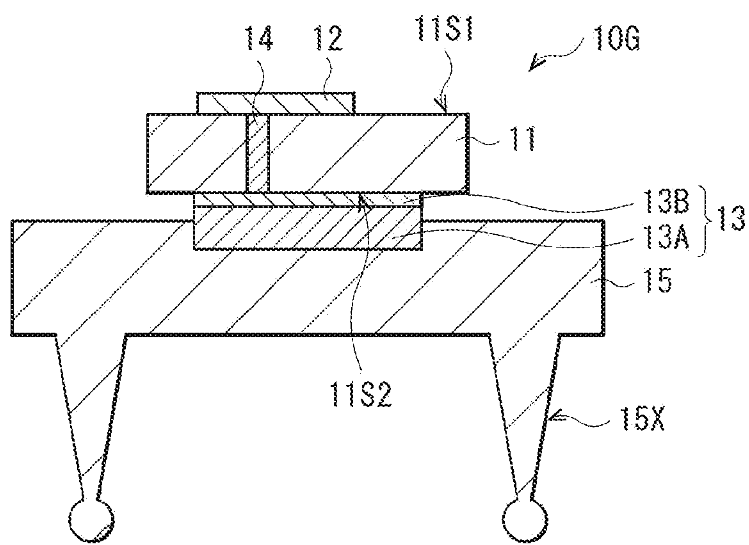
FIG. 12 is a cross-sectional schematic diagram illustrating a configuration of a biopotential measurement electrode according to Modification Example 7 of the present disclosure.

In addition, unlike in Modification Example 6 described above, a part of the first conductive portion 13A may be embedded in the measurement electrode 15 as in a biopotential measurement electrode 10G illustrated in FIG. 12. Further, the configurations of the first conductive portion 13A and the second conductive portion 13B may be inverted. Specifically, the second conductive portion 13B may be a magnet, whereas the first conductive portion 13A may include a ferromagnet.

3. Application Examples

Next, description will be made on specific examples (application examples) of the biological information measurement device 1 including a biopotential measurement electrode of the present disclosure (for example, the biopotential measurement electrode 10). However, configurations of the application examples described below are merely by way of example and the configurations can be changed, if necessary.

Figure 13:
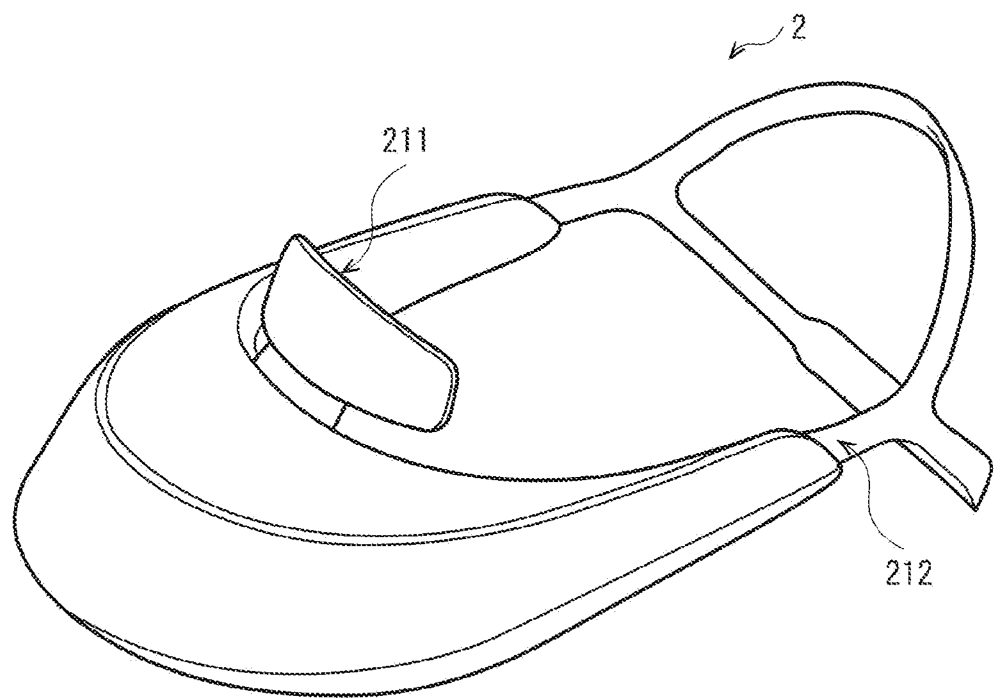
FIG. 13 is a diagram illustrating an example of a biological information measurement device.
Figure 14:
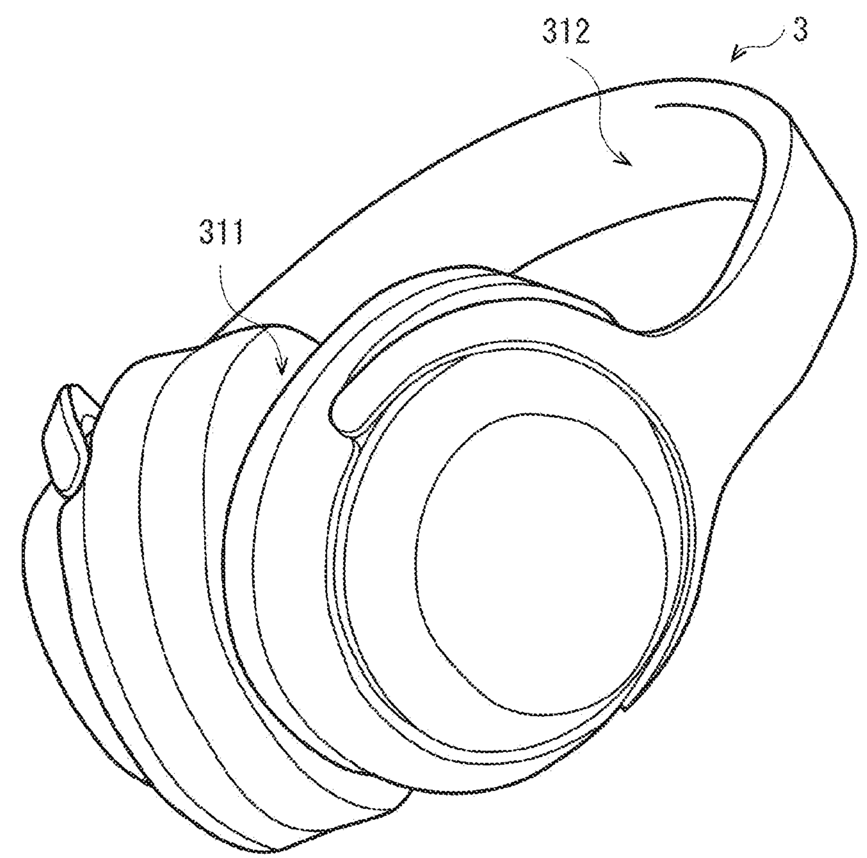
FIG. 14 is a diagram illustrating another example of the biological information measurement device.
Figure 15:
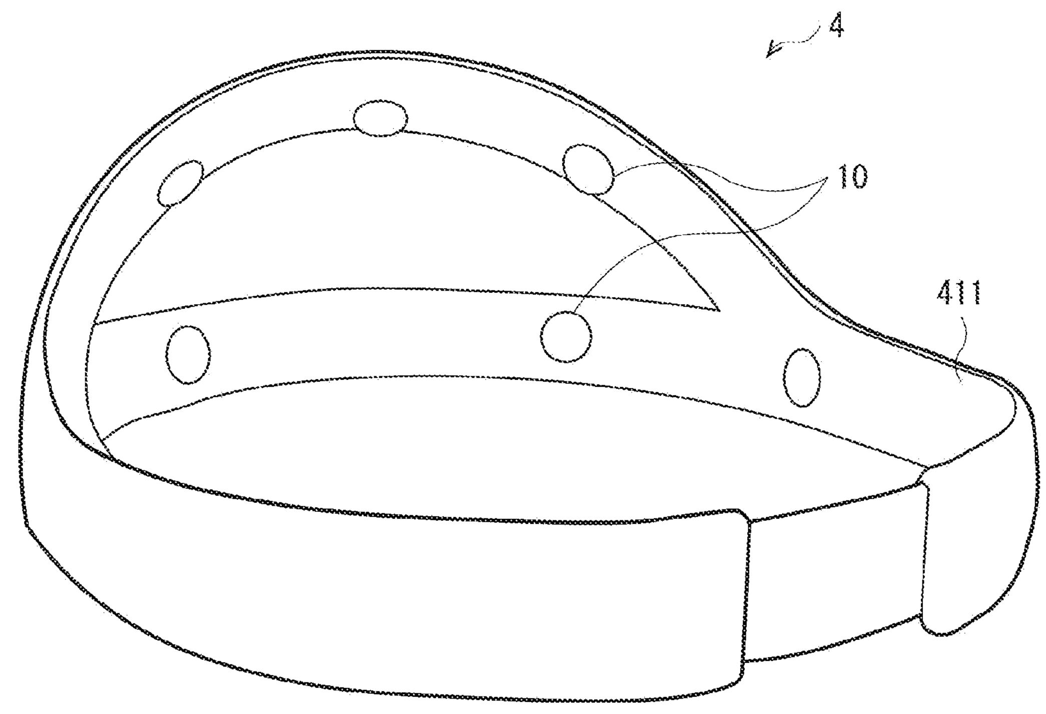
FIG. 15 is a diagram illustrating still another example of the biological information measurement device.
Figure 16:
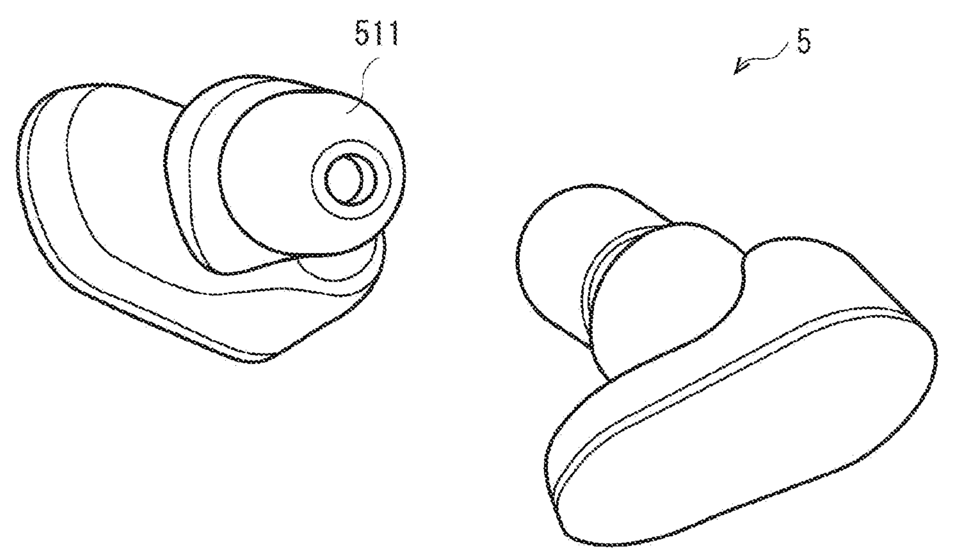
FIG. 16 is a diagram illustrating yet another example of the biological information measurement device.

The biopotential measurement electrode 10 can be installed within, for example, a pad unit 211 or a band unit 212 of a head mounted display 2 illustrated in FIG. 13. In addition to the above, the biopotential measurement electrode 10 can be installed within, for example, a pad unit 311 or a band unit 312 of a headphone 3 illustrated in FIG. 14. The biopotential measurement electrode 10 can be installed within, for example, a band unit 411 of the headband 4 illustrated in FIG. 15. The biopotential measurement electrode 10 can be installed within, for example, an earpiece 511 of an earphone 5 illustrated in FIG. 16.

Figure 17:
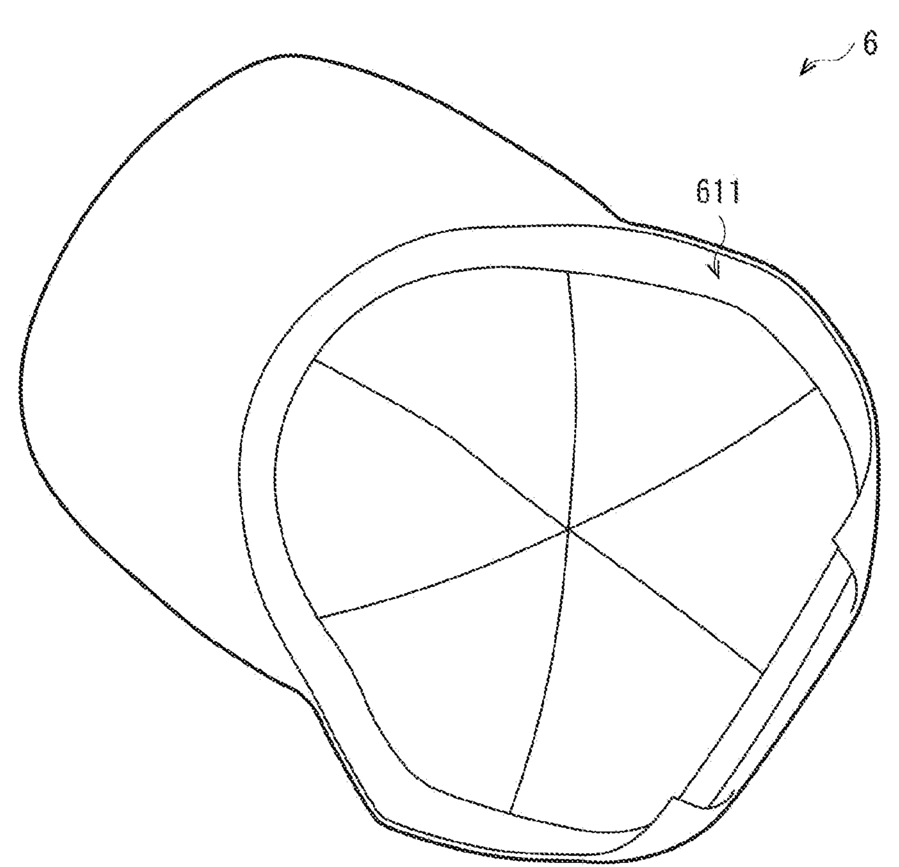
FIG. 17 is a diagram illustrating a further example of the biological information measurement device.

In addition, the biopotential measurement electrode 10 may be used for, for example, accessories such as clock (watch), bag, clothing, cap, glasses, and shoes in addition to wearable equipment. For example, the biopotential measurement electrode 10 can be installed in a ribbon 611 inside a cap 6 illustrated in FIG. 17.

Hereinabove, the present disclosure is described with reference to the embodiment, Modification Examples 1 to 7, and application examples; however, the present disclosure is not limited to the mode described in the above-described embodiment or the like and can be modified in a variety of manners. For example, the example using the plate-shaped substrate 11 is provided in the above-described embodiment or the like; however, for example, a doughnut-shaped substrate having an opening inside may be used. This causes a contact surface with the measurement electrode 15 to be formed also inside the substrate 11, which makes it possible to couple the substrate 11 and the measurement electrode 15 with a further stability. Therefore, it is possible to further improve the reliability.

In addition, it is not necessary to include all the components described in the above-described embodiment or the like and another component may also be further included. In addition, the above-described materials or the like of the components are merely by way of example and the described ones are not limiting.

It should be noted that the effects described herein are merely by way of example and another effect is also possible.

It should be noted that the present disclosure can have the following configuration as well. According to the present technology with the following configuration, at least a part of a first electrode unit disposed on a substrate where an electrical circuit is mounted is embedded in a second electrode unit having conductivity and elasticity and that is to be brought into contact with a living body. This causes a substrate side and the second electrode to be in contact at a plurality of contact surfaces, which makes it possible to improve an electrical and mechanical reliability in a user-friendly form.

(1)

A biopotential measurement electrode including:

a substrate on which an electrical circuit is mounted;

a first electrode unit disposed on the substrate and electrically coupled to the electrical circuit; and a second electrode unit having conductivity and elasticity and in which at least a part of the first electrode unit is embedded, the second electrode unit being to be brought into contact with a living body.

(2)

The biopotential measurement electrode according to (1), in which the substrate has a first surface on which the electrical circuit is mounted, a second surface opposite the first surface, and a third surface corresponding to a side surface between the first surface and the second surface.

(3)

The biopotential measurement electrode according to (2), in which the first electrode unit is disposed on the second surface of the substrate and the electrical circuit and the first electrode unit are electrically coupled through a through electrode penetrating between the first surface and the second surface of the substrate.

(4)

The biopotential measurement electrode according to (3), in which the first electrode unit is formed to extend from the second surface to the third surface of the substrate.

(5)

The biopotential measurement electrode according to (3), in which the first electrode unit is formed to extend from the second surface to a periphery of the first surface of the substrate.

(6)

The biopotential measurement electrode according to (2) or (3), in which the first electrode unit extends from the second surface to a periphery of the first surface of the substrate and a part of the first electrode unit disposed on the first surface extends to the electrical circuit to be electrically coupled to the electrical circuit.

(7)

The biopotential measurement electrode according to any one of (1) to (6), in which at least a part of the substrate is further embedded in the second electrode unit.

(8)

The biopotential measurement electrode according to any one of (1) to (7), further including a passivation film covering a front surface of the electrical circuit, in which the first electrode unit, the substrate, and the electrical circuit are embedded in the second electrode unit.

(9)

The biopotential measurement electrode according to any one of (2) to (8), in which the first electrode unit includes a first conductive portion embedded in the second electrode unit and a second conductive portion disposed on the second surface of the substrate.

(10)

The biopotential measurement electrode according to (9), in which the first conductive portion and the second conductive portion each include a magnetic conductive body.

(11)

The biopotential measurement electrode according to (10), in which one of the first conductive portion and the second conductive portion includes a ferromagnet.

(12)

The biopotential measurement electrode according to any one of (1) to (11), in which the second electrode unit has a plurality of projections on a contact surface for the living body.

(13)

The biopotential measurement electrode according to any one of (1) to (12), in which the second electrode unit includes a resin including PEDOT-PSS, polypyrrole, polyacetylene, polyphenylvinylene, polythiol, polyaniline, or an analog of PEDOT-PSS, polypyrrole, polyacetylene, polyphenylvinylene, polythiol, or polyaniline.

(14)

The biopotential measurement electrode according to any one of (1) to (12), in which the second electrode unit includes a resin including a metal particle, a metal sulfide, a metal selenide, or a metal chloride.

(15)

A biological information measurement device including biopotential measurement electrode, the biopotential measurement electrode including:

a substrate on which an electrical circuit is mounted;

a first electrode unit disposed on the substrate and electrically coupled to the electrical circuit; and a second electrode unit having conductivity and elasticity and in which at least a part of the first electrode unit is embedded, the second electrode unit being to be brought into contact with a living body.

The present application claims the benefit of Japanese Patent Application No. 2021-032893 filed with the Japan Patent Office on Mar. 2, 2021, the entire contents of which are incorporated herein by reference.

It should be understood by those skilled in the art that various modifications, combinations, sub-combinations, and alterations may occur depending on design requirements and other factors insofar as they are within the scope of the appended claims or the equivalents thereof.

What is claimed is:

1. A biopotential measurement electrode, comprising:

a substrate having a first axial or longitudinal surface and a second axial or longitudinal surface opposite the first axial or longitudinal surface;

an electrical circuit disposed directly on the first axial or longitudinal surface of the substrate;

a first electrode unit formed of a material having conductivity, wherein the first electrode unit is disposed on an entirety of the second axial or longitudinal surface of the substrate and is electrically coupled to the electrical circuit; and a second electrode unit having a first axial or longitudinal axial surface and a second axial or longitudinal surface opposite the first axial or longitudinal surface of the second electrode unit, wherein:

the second electrode unit is formed of a material having conductivity and elasticity;

at least a part of the first electrode unit is embedded in the material of the second electrode unit and is further disposed between the second axial or longitudinal surface of the substrate and the first axial or longitudinal surface of the second electrode unit; and at least a portion of the second electrode unit including the second axial or longitudinal surface thereof is configured for being brought into contact with a living body; and wherein the substrate has a third surface corresponding to a side surface of the substrate extending between the first axial or longitudinal surface of the substrate and the second axial or longitudinal surface of the substrate around a periphery of the substrate, and wherein the first electrode unit is further disposed on the third surface of the substrate.

2. The biopotential measurement electrode according to claim 1, wherein the electrical circuit and the first electrode unit are electrically coupled through a through electrode penetrating between the first axial or longitudinal surface of the substrate and the second axial or longitudinal surface of the substrate.

3. The biopotential measurement electrode according to claim 1, wherein the first electrode unit is further disposed on a portion of the first axial or longitudinal surface of the substrate to extend thereon from another portion of the first electrode unit disposed on the third surface, and wherein the first electrode unit disposed on the portion of the first axial or longitudinal surface of the substrate is electrically coupled to the electrical circuit.

4. The biopotential measurement electrode according to claim 1, further comprising a passivation film covering an axial or longitudinal surface of the electrical circuit opposite the first axial or longitudinal surface of the substrate, wherein an entirety of the first electrode unit, the substrate, and the electrical circuit are embedded in the material of the second electrode unit.

5. The biopotential measurement electrode according to claim 1, wherein the first electrode unit includes a first conductive portion embedded in the material of the second electrode unit and a second conductive portion disposed on the second axial or longitudinal surface of the substrate.

6. The biopotential measurement electrode according to claim 1, wherein the second electrode unit has a plurality of projections extending away from the second axial or longitudinal surface of the second electrode unit to thereby provide a contact surface for being brought into contact with the living body.

7. The biopotential measurement electrode according to claim 1, wherein the material of the second electrode unit includes:

a resin including PEDOT-PSS, polypyrrole, polyacetylene, polyphenylvinylene, polythiol, polyaniline; or an analog of: PEDOT-PSS, polypyrrole, polyacetylene, polyphenylvinylene, polythiol, or polyaniline.

8. The biopotential measurement electrode according to claim 1, wherein the material of the second electrode unit includes a resin including a metal particle, a metal sulfide, a metal selenide, or a metal chloride.

9. The biopotential measurement electrode according to claim 1, wherein material of the second electrode unit includes a thermoelastic polyurethane elastomer having conductive particles kneaded therein to a composition of 30 percent by weight.

10. The biopotential measurement electrode according to claim 1, wherein the electrical circuit is disposed directly on just a portion of the first axial or longitudinal surface of the substrate.

11. The biopotential measurement electrode according to claim 1, wherein the first electrode unit is electrically coupled to the second electrode unit by way of the first axial or longitudinal surface of the second electrode unit and a second axial or longitudinal surface of the first electrode unit.

12. The biopotential measurement electrode according to claim 1, wherein at least one of:

the first electrode unit consists essentially of a conductive metal material;

the second electrode unit is formed continuously of the material of the second electrode unit;

the material of the second electrode unit is different from the material of the first electrode unit; and the material of the second electrode unit consists essentially of a conductive material.

13. The biopotential measurement electrode according to claim 1, wherein at least a part of the substrate is embedded in the material of the second electrode unit along with the at least a part of the first electrode unit.

14. The biopotential measurement electrode according to claim 13, wherein the part of the substrate embedded in the material of the second electrode unit includes an entirety of the second axial or longitudinal surface of the substrate and at least portion of a third radial or lateral surface of the substrate.

15. A biological information measurement device comprising biopotential measurement electrode, the biopotential measurement electrode including:

a substrate having a first axial or longitudinal surface and a second axial or longitudinal surface opposite the first axial or longitudinal surface;

an electrical circuit disposed directly on the first axial or longitudinal surface of the substrate;

a first electrode unit formed of a material having conductivity, wherein the first electrode unit it disposed on an entirety of the second axial or longitudinal surface of the substrate and is electrically coupled to the electrical circuit; and a second electrode unit having a first axial or longitudinal axial surface and a second axial or longitudinal surface opposite the first axial or longitudinal surface of the second electrode unit, wherein:

the second electrode unit is formed of a material having conductivity and elasticity;

at least a part of the first electrode unit is embedded in the material of the second electrode unit and is further disposed between the second axial or longitudinal surface of the substrate and the first axial or longitudinal surface of the second electrode unit; and at least a portion of the second electrode unit including the second axial or longitudinal surface thereof is configured for being brought into contact with a living body in use of the biopotential measurement electrode; and wherein the substrate has a third surface corresponding to a side surface of the substrate extending between the first axial or longitudinal surface of the substrate and the second axial or longitudinal surface of the substrate around a periphery of the substrate, and wherein the first electrode unit is further disposed on the third surface of the substrate.

* * * * *